(12) United States Patent
Klomp

(10) Patent No.: US 9,867,928 B2
(45) Date of Patent: Jan. 16, 2018

(54) DEVICE FOR ADJUSTING THE IRRIGATION PRESSURE IN EYE OPERATIONS

(71) Applicant: EOS GMBH, Eschweiler (DE)

(72) Inventor: Manfred Klomp, AM Hulsberg (NL)

(73) Assignee: EOS GMBH, Eschweiler (DE)

( * ) Notice: Subject to any disclaimer, the term of this patent is extended or adjusted under 35 U.S.C. 154(b) by 89 days.

(21) Appl. No.: 14/405,379

(22) PCT Filed: May 8, 2013

(86) PCT No.: PCT/EP2013/059647
§ 371 (c)(1),
(2) Date: Dec. 3, 2014

(87) PCT Pub. No.: WO2013/185985
PCT Pub. Date: Dec. 19, 2013

(65) Prior Publication Data
US 2015/0133895 A1 May 14, 2015

(30) Foreign Application Priority Data

Jun. 12, 2012 (EP) .................... 12171667

(51) Int. Cl.
*A61M 31/00* (2006.01)
*A61M 3/02* (2006.01)
(Continued)

(52) U.S. Cl.
CPC ........... *A61M 3/0254* (2013.01); *A61F 9/007* (2013.01); *A61M 3/0241* (2013.01);
(Continued)

(58) Field of Classification Search
CPC .............. A61M 3/0241; A61M 3/0254; A61M 1/0058; A61M 2205/3344;
(Continued)

(56) References Cited

U.S. PATENT DOCUMENTS

| 4,655,197 A | 4/1987 | Atkinson |
| 5,322,506 A * | 6/1994 | Kullas ................. A61M 3/0233 604/153 |

(Continued)

FOREIGN PATENT DOCUMENTS

| EP | 0544410 | 6/1993 |
| EP | 1428541 | 6/2004 |
| WO | WO2009112251 | 9/2009 |

*Primary Examiner* — Emily Schmidt
(74) *Attorney, Agent, or Firm* — Workman Nydegger

(57) ABSTRACT

The invention relates to a device (1) for use in eye surgery, comprising a container (9) with fluid (5) which is connected via an irrigation line (12) to a surgical handpiece for delivering the fluid (5) for rinsing an eye (3) on which surgery has been performed, wherein a pillar (8), which in particular is electrically adjustable in its height, is provided for supporting the container (9) and for adjusting the height (H) between the container (9) and the surgical handpiece, and wherein a control for adjusting the height of the pillar (8) is provided in order to deliver the fluid (5) from the surgical handpiece into the eye (3) at an irrigation pressure predetermined by the surgeon, wherein pressurizing means (10) are provided which are designed for charging the fluid (5) to be delivered from the container (9) to the irrigation line (12) with an atmospheric overpressure ($P_{ATÜ}$) and wherein the control for adjusting the desired irrigation pressure is designed both for adjusting the height (H) of the pillar (8) and for adjusting the atmospheric overpressure ($P_{ATÜ}$) to be charged.

13 Claims, 2 Drawing Sheets

(51) Int. Cl.
 *A61F 9/007* (2006.01)
 *A61M 1/00* (2006.01)

(52) U.S. Cl.
 CPC ......... *A61M 1/0058* (2013.01); *A61M 3/0266* (2013.01); *A61M 2205/3331* (2013.01); *A61M 2205/3344* (2013.01); *A61M 2209/082* (2013.01); *A61M 2210/0612* (2013.01)

(58) Field of Classification Search
 CPC ........... A61M 2209/082; A61M 3/0266; A61F 9/007; A61F 9/00736
 See application file for complete search history.

(56) References Cited

U.S. PATENT DOCUMENTS

| | | |
|---|---|---|
| 5,505,707 A | 4/1996 | Manzie et al. |
| 2001/0023331 A1 | 9/2001 | Kanda et al. |
| 2004/0106915 A1* | 6/2004 | Thoe .................. A61B 17/00 606/1 |

* cited by examiner

DEVICE FOR ADJUSTING THE IRRIGATION PRESSURE IN EYE OPERATIONS

The invention relates to a device for use in eye surgery, comprising a container with fluid which is connected via an irrigation line to a surgical handpiece for delivering the fluid for rinsing an eye on which surgery has been performed, wherein a pillar, which in particular is electrically adjustable in its height, is provided for supporting the container and for adjusting the height between the container and the surgical handpiece, and wherein a control for adjusting the height of the pillar is provided in order to deliver the fluid from the surgical handpiece into the eye at an irrigation pressure predetermined by the surgeon.

Document EP 1 428 541 B1 discloses such a device which is part of an eye surgery device, by means of which a new lens can be inserted into the eye of a patient. During the surgery, at first a cut is placed on the eye by the surgeon, via which the old lens, which has been divided into small pieces, is removed and, subsequently, the new lens is introduced into the eye. In order to facilitate the removal of the small pieces of the old lens and to prevent the volume in the eye originally occupied by the old lens from collapsing during the surgery, the fluid must be delivered from the surgical handpiece into the eye on which surgery has been performed at an irrigation pressure. An irrigation pressure which is too high would permanently damage the eye, and at an irrigation pressure which is too low the eye is in danger of collapsing, for which reason the surgeon has to be able to adjust the appropriate irrigation pressure. In doing so, it is crucial how well the surgeon succeeds in the intended length of the cut on the eye, since said length influences the volume of the fluid per unit of time for rinsing the eye and the pressure conditions in the eye during the surgery. According to currently known surgery methods using the known device, the height of the pillar is therefore adjusted once by the surgeon after the cut has been performed on the eye and, thus, the irrigation pressure of the rinsing fluid is predetermined by the surgeon.

In the known device, it has turned out to be disadvantageous that the height of the pillar is adjustable only to a certain extent and, in case of a particularly large cut in the eye, the required irrigation pressure cannot be achieved even with a maximum height of the pillar. It may also be that the maximum height adjustable with the pillar would indeed be enough, but that the height of the pillar as required for the desired irrigation pressure is not adjustable in the operating room due to constructional limitations such as, for example, the ceiling height.

The invention is based on the object of providing a device for use in eye surgery which provides greater flexibility and security to the surgeon for adjusting the irrigation pressure of the fluid in the eye which is required for the eye surgery and non-hazardous to health.

According to the invention, said problem is solved in that pressurizing means are provided which are designed for charging the fluid to be delivered from the container to the irrigation line with an atmospheric overpressure and that the control for adjusting the desired irrigation pressure is designed both for adjusting the height of the pillar and for adjusting the atmospheric overpressure to be charged.

In this way, the advantage is obtained that a certain minimum irrigation pressure of the fluid which, in any case, is required for the surgery is achieved by charging the atmospheric overpressure to the fluid using the pressurizing means. The fine adjustment or the final adjustment, respectively, of the desired irrigation pressure is effected via the control by adjusting the height of the pillar. Since, once charged, an atmospheric overpressure can be reduced only by the fluid which flows off slowly or by means of a relatively expensive infusion set, this graduated buildup of the irrigation pressure yields the advantage that a certain minimum irrigation pressure is provided by charging the atmospheric overpressure, which irrigation pressure can be adjusted properly and reliably and also readjusted via the simple and immediately effective height adjustment of the pillar.

Further advantageous embodiments of the system according to the invention are illustrated below in further detail by way of the figures.

Figure 1:
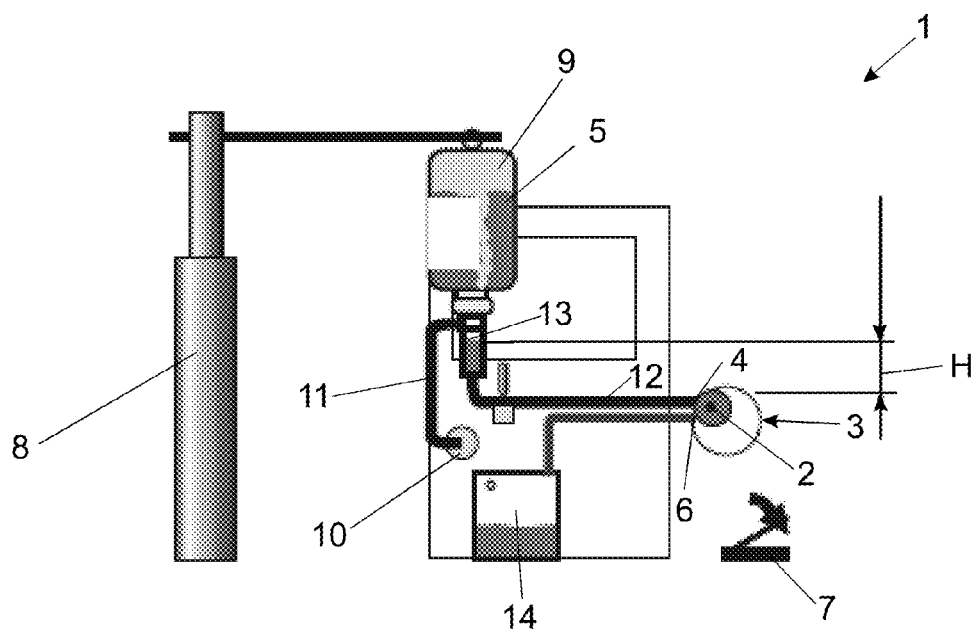
FIG. 1 shows a device for use in eye surgery.
Figure 2:
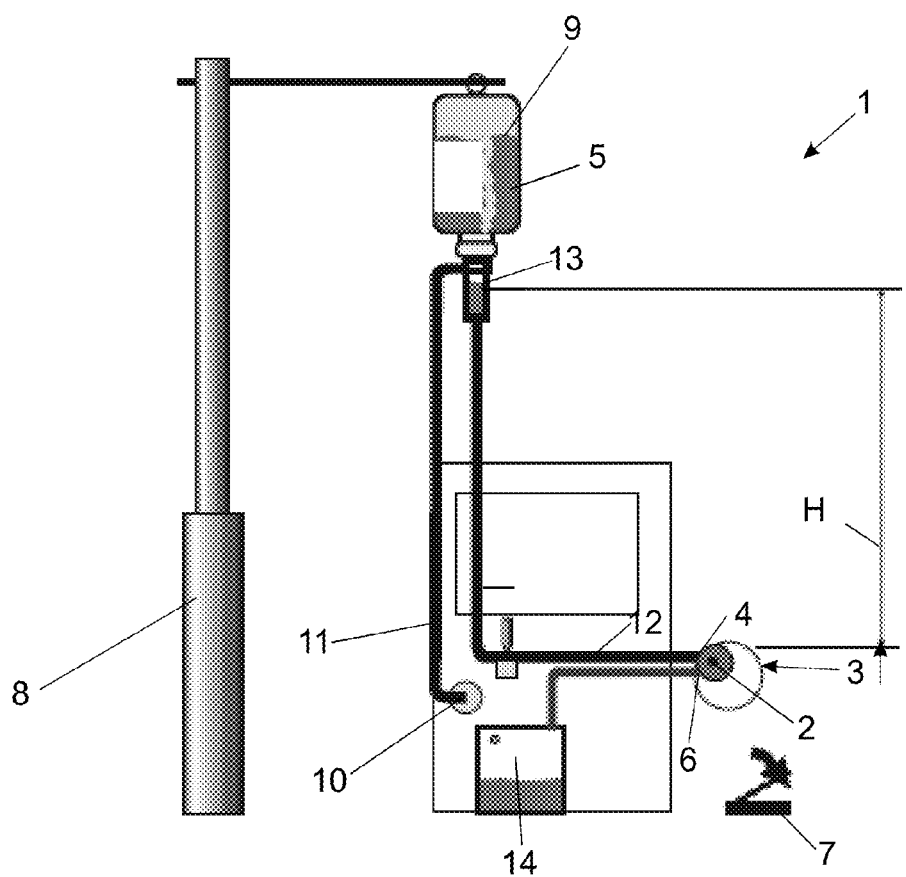
FIG. 2 shows the device according to FIG. 1, wherein the height of the pillar of the container has been altered.

FIG. 1 shows a device 1 for use in eye surgery which forms part of an eye surgery device which is not illustrated in further detail in FIG. 1. Using the eye surgery device, a new lens 2 can be inserted into an eye 3 of a patient. During the surgery, at first a cut is placed on the eye 3 by the surgeon.

A surgical handpiece, which is not illustrated in further detail in FIG. 1, fulfills three functions during the surgery. At an irrigation opening 4, fluid or rinsing fluid 5, respectively, for rinsing the eye 3 is delivered from the surgical handpiece into the eye 3 at an irrigation pressure predetermined by the surgeon. A knife provided in the surgical handpiece and driven by a piezo divides the old lens 2 into small pieces which are sucked in together with the rinsing fluid 5 via an aspiration opening 6 of the handpiece and are collected in a cartridge 14 of the eye surgery device.

In order to facilitate the removal of the small pieces of the old lens 2 and to prevent the volume in the eye 3 originally occupied by the old lens 2 from collapsing during the surgery, the rinsing fluid 5 must be delivered from the surgical handpiece into the eye 3 on which surgery has been performed at a certain predetermined irrigation pressure. An irrigation pressure which is too high would permanently damage the eye 3, and at an irrigation pressure which is too low the eye 3 is in danger of collapsing, for which reason the surgeon has to adjust the appropriate irrigation pressure. In doing so, it is crucial how well the surgeon succeeds in the intended length of the cut on the eye at the start of the surgery, since said length influences the volume of the rinsing fluid 5 per unit of time for rinsing the eye 3.

The device 1 now has a foot switch 7 by means of which the surgeon is able to predetermine both the momentarily desired irrigation pressure and the momentarily desired negative pressure for suction at the aspiration opening 6. Furthermore, the device 1 comprises a control not illustrated in further detail in the figures which is implemented by a computer including a computer program of the device 1 and, as described below, adjusts both the predetermined irrigation pressure at the irrigation opening 4 and the predetermined negative pressure at the aspiration opening 6.

For adjusting the irrigation pressure, the device 1 now comprises both a pillar 8 for the container 9 of the rinsing fluid 5, which pillar is electrically adjustable in its height, and pressurizing means 10 which charge an atmospheric overpressure via a pressure line 11 onto a surface 13 of the rinsing fluid 5 to be delivered to the irrigation line 12. The control actuates the electric motor of the pillar 8 in order to adjust a particular height H of the fluid column from the container 9 to the irrigation opening 4 of the surgical handpiece. The height H of the fluid column influences the irrigation pressure at the irrigation opening 4. The pressurizing means 10 formed by an electric pneumatic pump pump compressed air onto the surface 13 of the fluid column at an atmospheric overpressure predetermined by the control, whereby the irrigation pressure is increased additionally.

Figure 3:
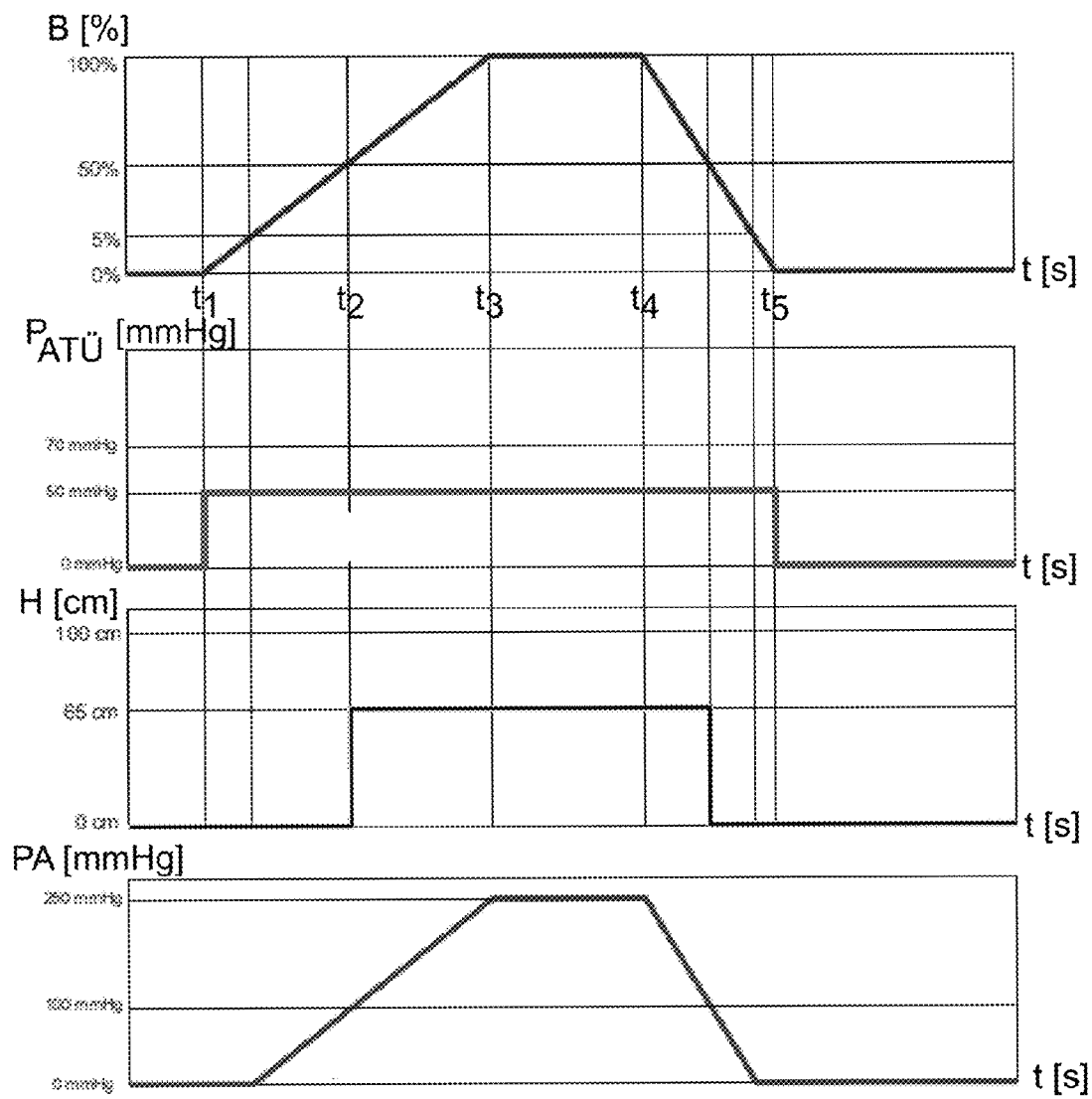
FIG. 3 shows how the control of the device according to FIG. 1 adjusts the irrigation pressure predetermined by a foot switch.

In FIG. 3, four graphs are depicted which show how the control meets those demands. In the uppermost graph, a possible actuation B of the foot switch 7 over time t is illustrated. Up to an instant $t_1$, the surgeon does not actuate the foot switch and, as from said instant $t_1$, starts to actuate the foot switch 7 more and more strongly until he or she depresses the foot switch 7 by 50% at instant $t_2$ and completely, that is by 100%, at instant $t_3$. From instant $t_4$ to instant $t_5$, the surgeon presses the foot switch 7 more and more slightly.

In a graph illustrated underneath, the atmospheric overpressure $P_{ATÜ}$ by the pressurizing means 10, which has been predetermined by the control as a result of the surgeon's actuation B of the foot switch 7, is illustrated according to a first exemplary embodiment. According to said exemplary embodiment, a pressure of 50 mmHg is charged by the pressurizing means 10 via the pressure line 11 onto the surface 13 of the rinsing fluid 5 to be delivered to the irrigation line 12 already upon a slight actuation of the foot switch 7, already from an actuation B of 1%. Said atmospheric overpressure $P_{ATÜ}$ is maintained by the control for as long as the actuation B of the foot switch amounts to more than 1%.

In a graph illustrated underneath, the adjustment of the height H between the surface 13 in the container 9 and the irrigation opening 4 of the surgical handpiece by means of the control, depending on the actuation B of the foot switch 7 by the surgeon, is illustrated. At instant $t_3$ when the foot switch is being actuated by 50%, the control brings the electrically adjustable pillar 8 from a height of H=0 cm to height H=65 cm. A height H=100 cm fluid column roughly corresponds to a pressure of 73.5 mmHg, for which reason, as from instant $t_3$, the irrigation pressure of the rinsing fluid at the irrigation opening 4 adds up from 50 mmHg+48 mmHg to a total of 98 mmHg. Said irrigation pressure predetermined by the surgeon via the actuation B of the foot switch 7 is maintained by the control for as long until the surgeon actuates the foot switch 7 again with less force than 50%. For this purpose, the control reduces the height H of the pillar 8.

In the lowermost graph in FIG. 3, the negative pressure PA of the aspiration which is generated by a suction pump of the device 1 not illustrated in further detail in the figures and is controlled by the control according to said graph is illustrated. According to said exemplary embodiment, the negative pressure is evenly increased by the control if the foot switch 7 is actuated in a consistently increasing manner. This has proved to be advantageous because, with an increasing actuation of the foot switch 7, also the knife in the handpiece is driven more strongly by the piezo and, thus, more biological material accumulates, which has to be aspirated through the aspiration opening 6 into the cartridge 14.

By means of the control according to the invention for setting the desired irrigation pressure both by adjusting the height H of the pillar 8 and by charging the surface 13 with the atmospheric overpressure $P_{ATÜ}$, the advantage is obtained that, by charging the atmospheric overpressure $P_{ATÜ}$, a certain minimum irrigation pressure is provided which can be adjusted properly and reliably and also readjusted via the simple and immediately effective height adjustment of the pillar 8. Depending on which atmospheric overpressure is predetermined by the control, only a small additional pressure increase by slightly changing the height of the pillar 8 is necessary. As a result, constructional limitations in the operating room can also not influence the buildup of the required irrigation pressure.

For the surgeon, it is particularly important that, during the surgery, the three functions of the surgical handpiece can be adjusted reliably and reproducibly by the control according to his or her requirements set by the foot switch 7. Consequently, a permanent change in the height H of the pillar 8 with any minor modification of the actuation B of the foot switch 7 would be very disruptive. Thus, it has proved to be advantageous to change the irrigation pressure only by gradually increasing the height H of the pillar 8, since the surgeon can thus get adapted to uniform pressure conditions, apart from time periods in which the pillar is just changing its height H, which substantially facilitates the surgery.

Depending on the exemplary embodiment, one or more steps (increasing the height H of the pillar 8) can be determined by the control at certain predetermined percentages of the actuation B of the foot switch 7. Similarly, also the pressurizing means 10 might at first apply an atmospheric overpressure $P_{ATÜ}$ of only, for example, 30 mmHg at, e.g., =5% and thus provide the surgeon with a larger control range with the foot switch 7 by adjusting the height of the pillar 8. Depending on the application, a person skilled in the art is able, according to the invention, to determine the best composition of those partial pressures via the atmospheric overpressure $P_{ATÜ}$ and the height adjustment. In this connection, various embodiments of the method of controlling the device 1 are feasible.

It may be mentioned that, in some examples of use, it may also be advantageous if the control at first adjusts the height of the pillar upon actuation of the foot switch and only then, upon a stronger actuation of the foot switch, increases the irrigation pressure further using the pressurizing means. It might also be possible to perform this alternately or at a different predetermined sequence.

The values indicated in the table according to claim 4 have proved to be particularly advantageous in practice in order to enable a good operation on the lens of the eye.

It may be mentioned that, in the previous exemplary embodiment, functions operated or controlled electrically may also be replaced by functions operated or controlled pneumatically. So, instead of by the electric pneumatic pump, the pressurizing means might be driven, for example, also by a compressed air wall or a pneumatic cylinder.

The invention claimed is:

1. A device for use in eye surgery, comprising:
   a container with fluid which is connected via an irrigation line to a surgical handpiece for delivering the fluid for rinsing an eye on which surgery has been or is being performed,
   a pillar electrically adjustable in its height and configured for supporting the container and for adjusting a height between the container and the surgical handpiece,
   a control for adjusting the height of the pillar in order to deliver the fluid from the surgical handpiece into the eye at an irrigation pressure predetermined by the surgeon, and
   pressurizing means designed for charging the fluid to be delivered from the container to the irrigation line with an atmospheric overpressure ($P_{ATO}$), a suction pump configured to generate a negative pressure in order to aspirate material and/or fluid from the eye, the suction pump being connected via an aspiration line to the surgical handpiece, and a foot switch for presetting the irrigation pressure, the foot switch being configured so that, upon actuation, the foot switch triggers the pressurizing means in order to charge the fluid with the atmospheric overpressure ($P_{ATO}$) and, upon a subsequent further actuation of the foot switch, the foot switch causes the control to adjust the height of the pillar to further increase the irrigation pressure, wherein the control is configured to both adjust the height of the pillar and adjust the atmospheric overpressure ($P_{ATO}$) of the fluid to be charged, wherein the control is also configured so as to, upon progressively increasing actuation of the foot switch, control the suction pump in order to evenly increase the negative pressure and gradually adjust the height of the pillar to increase irrigation pressure.

2. A device according to claim 1, wherein the control is configured, corresponding to the current position of the foot switch, to control the pressurizing means in order to charge the fluid with one of two or more different predetermined atmospheric overpressures ($P_{ATO}$).

3. A device according to claim 2, wherein the control is configured to control the pressurizing means in order to charge the atmospheric overpressure ($P_{ATO}$) as indicated below and to control the height between the container and the surgical handpiece as indicated below, upon a percent actuation of the foot switch as indicated below:

| Foot switch actuation [%] | Atmospheric overpressure ($P_{ATO}$) on fluid [mmHg] | Height between container and handpiece [cm] |
|---|---|---|
| 1 to 10 | 30 to 70 | 0 to 10 |
| 10 to 100 | 30 to 70 | 30 to 100 |

4. A device according to claim 3, wherein when the foot switch actuation % is 1 to 10, the atmospheric overpressure ($P_{ATO}$) on fluid is 50 mmHg and the height between the container and the handpiece is 0 cm.

5. A device according to claim 3, wherein when the foot switch actuation % is 10 to 100, the atmospheric overpressure ($P_{ATO}$) on fluid is 50 mmHg and the height between the container and the handpiece is adjusted to 60 to 70 cm.

6. A device according to claim 5, wherein when the foot switch actuation % is from 10 to 100, the height between the container and the handpiece is adjusted to 65 cm.

7. A device according to claim 1, wherein the control is configured, according to the current position of the foot switch, to bring the height of the pillar to one of two or more different predetermined heights.

8. A device according to claim 1, wherein the foot switch and control are configured and interact so that:

when the foot switch is actuated in a first position, the control causes the fluid to to be delivered to the surgical handpiece at a first pressure, causes the container to be at a first height, and causes the suction pump to generate a first negative pressure, wherein the first pressure is determined by at least the atmospheric overpressure ($P_{ATO}$);

when the foot switch is actuated in a second position greater than the first position, the control causes the container to be raised to a second height greater than the first height so that the fluid is delivered to the surgical handpiece at a second pressure greater than the first pressure, and causes the suction pump to generate a second negative pressure greater than the first negative pressure, wherein the second pressure is determined by the atmospheric overpressure ($P_{ATO}$) and the second height of the container; and when the foot switch is actuated in a third position greater than the second position, the control causes the container to be raised to a third height greater than the second height so that the fluid is delivered to the surgical handpiece at a third pressure greater than the second pressure, and causes the suction pump to generate a third negative pressure greater than the second negative pressure, wherein the third pressure is related to the atmospheric overpressure ($P_{ATO}$) and the third height of the container.

9. A method of controlling a device for eye surgery in order to adjust an irrigation pressure predetermined by a surgeon, comprising:

delivering a fluid from a container via an irrigation line into a surgical handpiece, the fluid being delivered from the surgical handpiece into an eye on which surgery has been or is being performed; and aspirating material and/or fluid from the eye via a negative pressure applied by a suction pump;

upon initial actuation of a foot switch, charging the fluid to be delivered from the container to the irrigation line with an atmospheric overpressure ($P_{ATO}$); and upon further actuation of the foot switch, electrically adjusting a height of a pillar supporting the container in order to adjust the predetermined irrigation pressure, wherein setting the predetermined irrigation pressure is thereby accomplished by both adjusting the height of the pillar and charging with the atmospheric overpressure ($P_{ATO}$), wherein the suction pump is controlled to evenly increase the negative pressure upon a progressively increasing actuation of the foot switch.

10. A method according to claim 9, further comprising readjusting the height of the pillar according to a current specification of the foot switch in stages.

11. A method according to claim 9, wherein:

when the foot switch is actuated in a first position, the fluid is delivered to the surgical handpiece at a first pressure, the container is at a first height, and the suction pump applies a first negative pressure, wherein the first pressure is determined by at least the atmospheric overpressure ($P_{ATO}$);

when the foot switch is actuated in a second position greater than the first position, the fluid is delivered to the surgical handpiece at a second pressure greater than the first pressure, and the suction pump applies a second negative pressure greater than the first negative pressure, wherein the second pressure is determined by the atmospheric overpressure ($P_{ATO}$) and the second height of the container; and when the foot switch is actuated in a third position greater than the second position, the fluid is delivered to the surgical handpiece at a third pressure greater than the second pressure, and the suction pump applies a third negative pressure greater than the second negative pressure, wherein the second pressure is determined by the atmospheric overpressure ($P_{ATO}$) and the third height of the container.

12. A device for use in eye surgery, comprising:
a container with fluid which is connected via an irrigation line to a surgical handpiece for delivering the fluid for rinsing an eye on which surgery has been or is being performed,
a pillar electrically adjustable in its height and configured for supporting the container and for adjusting a height between the container and the surgical handpiece,
an overpressure pump configured for charging the fluid to be delivered from the container to the irrigation line with an atmospheric overpressure ($P_{ATO}$),
a suction pump for generating a negative pressure for aspirating material and/or fluid from the eye, the suction pump being connected via an aspiration line to the surgical handpiece, and
a foot switch for controlling the irrigation pressure, the height of the pillar, and the suction pump, wherein the foot switch is configured so that, upon initial actuation, the foot switch triggers the overpressure pump to charge the atmospheric overpressure ($P_{ATO}$), upon a subsequent further actuation of the foot switch, the foot switch further increases the irrigation pressure by adjusting the height of the pillar, and upon progressively increasing actuation of the foot switch, the negative pressure generated by the suction pump is correspondingly progressively increased.

13. A device according to claim 12, wherein the foot switch is configured so that:
when the foot switch is actuated in a first position, the overpressure pump is actuated to deliver the fluid to the surgical handpiece at a first pressure equal to or greater than the atmospheric overpressure, causes the container to be at a first height, and causes the suction pump to generate a first negative pressure;
when the foot switch is actuated in a second position greater than the first position, the container is raised to a second height greater than the first height in order to deliver fluid to the surgical handpiece at a second pressure greater than the first pressure, and causes the suction pump to generate a second negative pressure greater than the first negative pressure; and
when the foot switch is actuated in a third position greater than the second position, the container is raised to a third height greater than the second height in order to deliver fluid to the surgical handpiece at a third pressure greater than the second pressure, and causes the suction pump to generate a third negative pressure greater than the second negative pressure.

* * * * *